United States Patent [19]

Goorden

[11] 4,308,385
[45] Dec. 29, 1981

[54] PROCESS FOR PURIFYING UREA-CONTAINING WASTE WATER AND PROCESS FOR PREPARING MELAMINE

[75] Inventor: Josephus J. P. M. Goorden, Sittard, Netherlands

[73] Assignee: Stamicarbon, B. V., Geleen, Netherlands

[21] Appl. No.: 147,714

[22] Filed: May 8, 1980

[30] Foreign Application Priority Data

May 9, 1979 [NL] Netherlands ........................ 7903623

[51] Int. Cl.$^3$ ...................... C01C 1/08; C07D 251/60
[52] U.S. Cl. ................................... 544/201; 423/358
[58] Field of Search ........................ 423/358; 544/201

[56] References Cited

U.S. PATENT DOCUMENTS

| | | | |
|---|---|---|---|
| 3,697,521 | 10/1972 | Van Nassau et al. ................ | 544/201 |
| 4,087,513 | 5/1978 | Schell .................................. | 423/358 |
| 4,120,667 | 10/1978 | Gettert et al. ....................... | 55/48 |
| 4,163,648 | 8/1979 | Biermans ............................. | 55/48 |

Primary Examiner—O. R. Veritz
Assistant Examiner—Wayne A. Langel
Attorney, Agent, or Firm—Cushman, Darby & Cushman

[57] ABSTRACT

An improved process for the removal of urea from urea-containing waste water by hydrolysis and desorption of the ammonia and carbon dioxide thus formed. Urea-containing waste water is treated in a process for the separation of ammonia and carbon dioxide from mixtures thereof, which process has (a) an ammonia separation zone wherefrom ammonia, substantially free of carbon dioxide and water, is obtained; (b) a carbon dioxide separation zone wherefrom carbon dioxide, substantially free of ammonia and water is obtained, and (c) a desorption zone wherefrom water, substantially free of carbon dioxide and ammonia is obtained. The urea is substantially completely hydrolyzed and the ammonia and carbon dioxide produced thereby can be recovered.

7 Claims, 2 Drawing Figures

PROCESS FOR PURIFYING UREA-CONTAINING WASTE WATER AND PROCESS FOR PREPARING MELAMINE

BACKGROUND OF THE INVENTION

This invention relates to a process for purifying urea-containing waste water by treating the waste water at an elevated temperature and pressure to hydrolyze the urea, and desorbing the ammonia and carbon dioxide thus formed.

In the preparation and processing of urea, a difficulty arises that the urea-containing waste water often obtained cannot be discharged as is to surface waters. Therefore various means have been attempted to remove the urea from this waste water.

Biological waste water purification constitutes a potential solution to this problem, but has a disadvantage that at least a two step purification is always necessary, that is, aerobic and anaerobic purification, and there is no possibility of recovering or recycling the urea or the ammonia that might otherwise be obtained.

Economically, it is preferred to remove and recover the urea and/or ammonia from the waste water. Various methods have been proposed to accomplish this, all of which basically involve the steps of desorbing ammonia and carbon dioxide from the urea-containing waste water, subsequently hydrolyzing the urea contained in the waste water followed by the total or partial desorption of the ammonia and carbon dioxde thus formed. A process of this nature is described in Proceedings, The Fertilizer Institute, Environmental Symposium, 13–16 January, 1976, p. 91 et seq.

However, such a process has the disadvantage that a separate installation consisting of a number of distillation and hydrolysis columns is required to process the urea-containing waste water.

An objective of the present invention is therefore to provide an improved method for the removal of urea from urea-containing waste water in an effective and economic manner. It is a further objective to provide for the removal of urea from urea-containing waste water without the necessity of installing special equipment solely for that purpose. It is a further objective to provide a method for the removal of urea from waste water by hydrolysis and recovering substantially pure ammonia and/or substantially pure carbon dioxide produced thereby.

SUMMARY OF THE INVENTION

These and other objectives are accomplished by the present invention by carrying out the hydrolysis of urea, and recovering ammonia and carbon dioxide formed, in apparatus utilized for the separation of ammonia and carbon dioxide from process streams containing mixtures thereof, simultaneously with the recovery of ammonia and carbon dioxide from such process streams. Specifically, the apparatus and method by which the urea-containing waste water is treated in accordance with the present invention involves the steps of (1) removal of an ammonia off-gas substantially free of carbon dioxide and water in an ammonia separation zone, (2) removal of a carbon dioxide off-gas, substantially free of ammonia and water, in a carbon dioxide separation zone, and (3) desorption of ammonia and carbon dioxide in a desorption zone yielding water substantially free of ammonia, carbon dioxide and urea.

The present invention is based on the surprising discovery that, under the conditions applied in such processes for the separation of mixtures of ammonia and carbon dioxide (such as temperature, liquid residence time, gas-liquid ratio and number of trays), and most specifically the conditions applied in the desorption zone, complete or substantially complete hydrolysis of urea, and desorption of the ammonia and carbon dioxide will occur so that the liquid discharged from the separation process is free or substantially free of urea, carbon dioxide and ammonia.

One difficulty encountered in the recovery of ammonia and carbon dioxide from mixtures thereof is that the binary system of ammonia and carbon dioxide forms a maximum boiling azeotrope at a molar ammonia-to-carbon dioxide ratio of about 2:1, and therefore cannot be separated by simple distillation. This phenomenon also occured in the ternary system of ammonia, carbon dioxide and water, and the term "azeotrope" as used herein should be understood to include this phenomenon in the ternary system as well. This system is described in P.J.C. Kassenbrood, Chemical Reaction Engineering, Proceedings of the Fourth European Symposium, Sept. 9–11, 1968, Pergamon Press (1971), p. 317–328.

As used herein, with respect to such binary or ternary mixtures, the term "rich" with respect to ammonia shall be understood to mean that when heat is applied to a mixture "rich" in ammonia, substantially pure gaseous ammonia escapes until the remaining mixture has a composition on the boundary line, that is at the azeotrope. Conversely, a mixture is considered "rich" with respect to carbon dioxide if, when heat is applied to such mixture, substantially pure carbon dioxide escapes. Once the liquid mixture composition is at the boundary line or azeotropic composition, further rectification or distillation at constant pressure results in a gaseous mixture of all components, but the composition of the remaining liquid mixture does not leave the boundary line.

Various methods have been proposed to get around this azeotrope, all of which entail the separation of the ammonia-carbon dioxide mixtures into their constituents. However the major processes for separating substantially pure ammonia and substantially pure carbon dioxide from mixtures thereof, which may also contain water, are of the type described in British Pat. No. 1,129,939, U.S. Pat. No. 4,163,648 and U.S. Pat. No. 4,120,667 the respective disclosures of which are hereby incorporated herein by reference in their entirety.

In British Pat. No. 1,129,939, a gas mixture consisting of ammonia and carbon dioxide, rich with respect to ammonia, is absorbed in water or an aqueous solution. Ammonia is distilled from the resulting aqueous solution at atmospheric pressure. The remainder of this solution is then subjected to fractional distillation at a pressure of between 5 and 20 atmospheres absolute with heating in order to remove the carbon dioxide. This process is based on the principle that changing the pressure of a system of ammonia, carbon dioxide and water makes it possible to separate out ammonia at the lower pressure and carbon dioxide at the higher pressure. In such a "pressure differential" type of process, the system pressure in the carbon dioxide separation zone should be at least twice that in the ammonia separation zone. Preferably the ratio between the system pressures in the ammonia separation and the carbon dioxide separation zones should be between about 1:5 and 1:20 if the separation is to proceed smoothly.

However, the pressure differential type of process has the drawback that if the ammonia and carbon dioxide mixture is available at a pressure of more than one atmosphere, it first has to be expanded to one atmosphere. Gaseous ammonia is then released having a maximum pressure of one atmosphere, or even lower in the event that a large amount of another gas is present. If this ammonia is to be subjected to further processing, such as in a urea synthesis process, it has to be raised to a higher pressure. The compression energy required for this is quite substantial. Furthermore, the carbon dioxide concentration in the ammonia has to be kept extremely low in order to avoid the formation and deposition of solid ammonium carbamate in the compressor and high pressure lines.

An alternative process not requiring such a pressure differential is disclosed in U.S. Pat. No. 4,163,648. The process therein described permits the recovery of ammonia and carbon dioxide separately from such mixtures, without the need for a pressure differential, and thus permits the direct recovery of ammonia at substantially higher pressures. This process is based on the principle that the azeotropic composition achieved in the ammonia separation zone can be moved away from the boundary line by the addition of dilution water to the carbon dioxide separation zone wherefrom substantially pure carbon dioxide can be recovered. Specifically, according to that disclosure, dilution water in an amount of between 0.2 and 6 times, by weight, the total weight of ammonia and carbon dioxide fed into the carbon dioxide separation zone is added thereto. For simplicity, this latter type of process will be referred to herein as a "dilution process".

According to one embodiment of such a dilution process, a mixture of ammonia, carbon dioxide and possibly water, rich with respect to ammonia, is initially fed into an ammonia separation zone wherefrom ammonia substantially free of carbon dioxide and water is separated. The residual liquid phase leaving the bottom of this ammonia separation zone is fed into the carbon dioxide separation zone, wherein it is diluted with between 0.2 and 6 times its weight in water. Carbon dioxide substantially free of ammonia and water is separated out, and the residual liquid phase from the bottom of the carbon dioxide separation zone is fed into the desorption zone wherein virtually all ammonia and carbon dioxide are desorbed and the resulting gas phase is introduced into the ammonia separation zone.

According to another embodiment of the dilution type of process, a mixture of ammonia, carbon dioxide and possibly water, which mixture is lean with respect to ammonia, is fed into a carbon dioxide separation zone wherefrom carbon dioxide substantially free of ammonia and water is separated. From the bottom of this carbon dioxide separation zone, the residual liquid phase is fed to a desorption zone wherein virtually all ammonia and carbon dioxide are desorbed and the resulting gas phase is introduced into the ammonia separation zone. Ammonia, substantially free of carbon dioxide and water, is recovered from this resulting gas phase in the ammonia separation zone, and the resulting liquid phase is supplied to the carbon dioxide separation zone. Diluting water is added to this carbon dioxide separation zone in an amount of between 0.2 and 6 times, by weight, the combined total weight of the initial mixture to be separated, plus the residual liquid phase from the ammonia separation zone fed into the carbon dioxide separation zone.

According to another embodiment of the dilution process, where the ammonia and carbon dioxide containing mixture to be separated also contains a substantial quantity of water, it may be advantageous to feed this mixture initially to the desorption zone wherein the ammonia and carbon dioxide are desorbed, and, together with some water vapor, are introduced into the ammonia separation zone. Ammonia, substantially free of carbon dioxide and water vapor, is obtained from the top of the ammonia separation zone, and the residual liquid phase, containing ammonia, carbon dioxide and water, is introduced into the carbon dioxide separation zone. Diluting water is also introduced into the carbon dioxide separation zone in an amount of between about 0.2 to 6 times, by weight, the total quantity of the residual liquid phase from the ammonia separation zone fed into the carbon dioxide separation zone. Carbon dioxide, substantially free of ammonia and water, is obtained from the top of the carbon dioxide separation zone, and the residual liquid phase from the bottom of the carbon dioxide separation zone is fed to the desorption zone.

Typically the ammonia and carbon dioxide mixtures separated in the aforementioned processes are gaseous process streams containing mixtures of ammonia and carbon dioxide, or are aqueous solutions of ammonia and carbon dioxide derived by scrubbing or absorbing ammonia and carbon dioxide out of such gaseous process streams with water. For instance in the synthesis of urea from ammonia and carbon dioxide at elevated temperature and pressure ammonium carbamate is removed from the reaction mixture by decomposition to carbon dioxide and ammonia, followed by removal of the ammonia and carbon dioxide by heating and/or stripping. The resulting gas phase can be treated as such, or as an aqueous solution, in the aforementioned separation processes. No urea would be present in such gaseous mixture or resulting solution.

Mixtures of ammonia and carbon dioxide are also formed in the preparation of melamine by the catalytic conversion of urea in the presence of gaseous ammonia or a gas mixture containing ammonia. After melamine is separated from the reaction mixture an aqueous solution containing ammonia and carbon dioxide is formed, which can be separated into substantially pure ammonia and substantially pure carbon dioxide by the aforementioned separation processes.

The present invention involves additionally treating urea-containing waste water in these separation processes, simultaneously with the separation of ammonia and carbon dioxide-containing process streams, and the discovery that under conditions therein applied with respect to temperature, liquid residence time, gas-liquid ratios and number of trays, substantially complete hydrolysis of the urea can be achieved, and substantially pure ammonia and substantially pure carbon dioxide can be recovered.

To obtain proper removal of urea from the urea-containing waste water, it is desirable that the desorption zone be operated at a pressure of between 5 and 50 bar. With lower pressures in the desorption zone, it is no longer possible to utilize a normal column for desorption. Instead, modified columns must be utilized having longer liquid residence times than in customary distillation columns. It is also possible to apply higher pressures than 50 bar, but this offers no additional advantages, and has the disadvantage that more corrosion resistance, and therefore more expensive materials, are required. Pressures of between 20 and 40 bar are preferably applied inasmuch as the process functions optimally at these pressures, and use can be made of normal or customary columns.

The temperatures maintained in the various separation zones depend on the pressures, the composition of the feed and the purity required of the products to be separated. In the dilution process, these temperatures, where rectifying columns are used in the separation zones, generally range within the limits stated in the following table:

|  | bottom | top |
|---|---|---|
| $NH_3$-separation | +60 to +170° C. | −35 to +66° C. |
| $CO_2$-separation | +75 to +200° C. | 0 to +100° C. |

The temperatures in the desorption zone are also determined by the pressures, the composition of the feed to the zone and the purity requirements (amount of ammonia and carbon dioxide) for the desorption water removed from the bottom of this zone. Generally these temperatures are chosen to be higher than the boiling point of the liquid phase to be desorbed at the pressures used.

The urea-containing waste water can be fed initially to any of the zones of the ammonia-carbon dioxide separation process. However, it is preferable to feed this urea-containing waste water initially to the carbon dioxide separation zone or the desorption zone inasmuch as it has been found that the total energy consumption of the process is less that if such feed is initially to the ammonia separation zone.

The urea-containing waste water treated in the present invention may, for instance, originate in a urea plant, a melamine plant or some other plant in which urea is used as feed stock, or is formed as a by-product or an intermediate. The invention relates particularly to the treatment of urea-containing process condensate originating from a urea synthesis plant. Such urea-containing process condensate is obtained by condensing a gas mixture containing urea, ammonia, carbon dioxide and water, or by absorbing such a urea-containing gas mixture in an aqueous liquid. Such a gas mixture may originate, for instance, in the step of concentrating an aqueous urea solution by evaporation to a concentrated or substantially water-free urea solution.

Another embodiment of the present invention involves a process for preparing melamine by the catalytic conversion of urea in the presence of gaseous ammonia or a gas mixture containing ammonia. The melamine is separated from the gaseous mixture thus formed, followed by the formation of an aqueous solution of ammonia, carbon dioxide and/or compounds thereof from the remaining gas mixture. This gas mixture is thereupon fed into a separation process as described above, and separated into substantially pure ammonia and substantially pure carbon dioxide. Additionally, urea-containing waste water is fed into the separation process, directly into the separation step from which substantially pure carbon dioxide is recovered, i.e., the carbon dioxide separation zone. More specifically, process condensate originating from the manufacture of urea that has been used at least in part as a feed stock for the preparation of melamine, is fed into this carbon dioxide separation zone for purposes of removal of the urea contained therein.

The advantage of the process of the present invention is that a separate processing section for the purification of urea-containing waste water and recovery of ammonia thus formed can be dispensed with in processes for the preparation or processing of urea. This urea-containing effluent can be fed in toto into an ammonia/carbon dioxide separation unit which also functions to separate mixtures of carbon dioxide and ammonia created in the preparation and/or processing of urea, or in the preparation of processing of products manufactured from urea, such as melamine.

DETAILED DESCRIPTION OF PREFERRED EMBODIMENT

Figure 1:
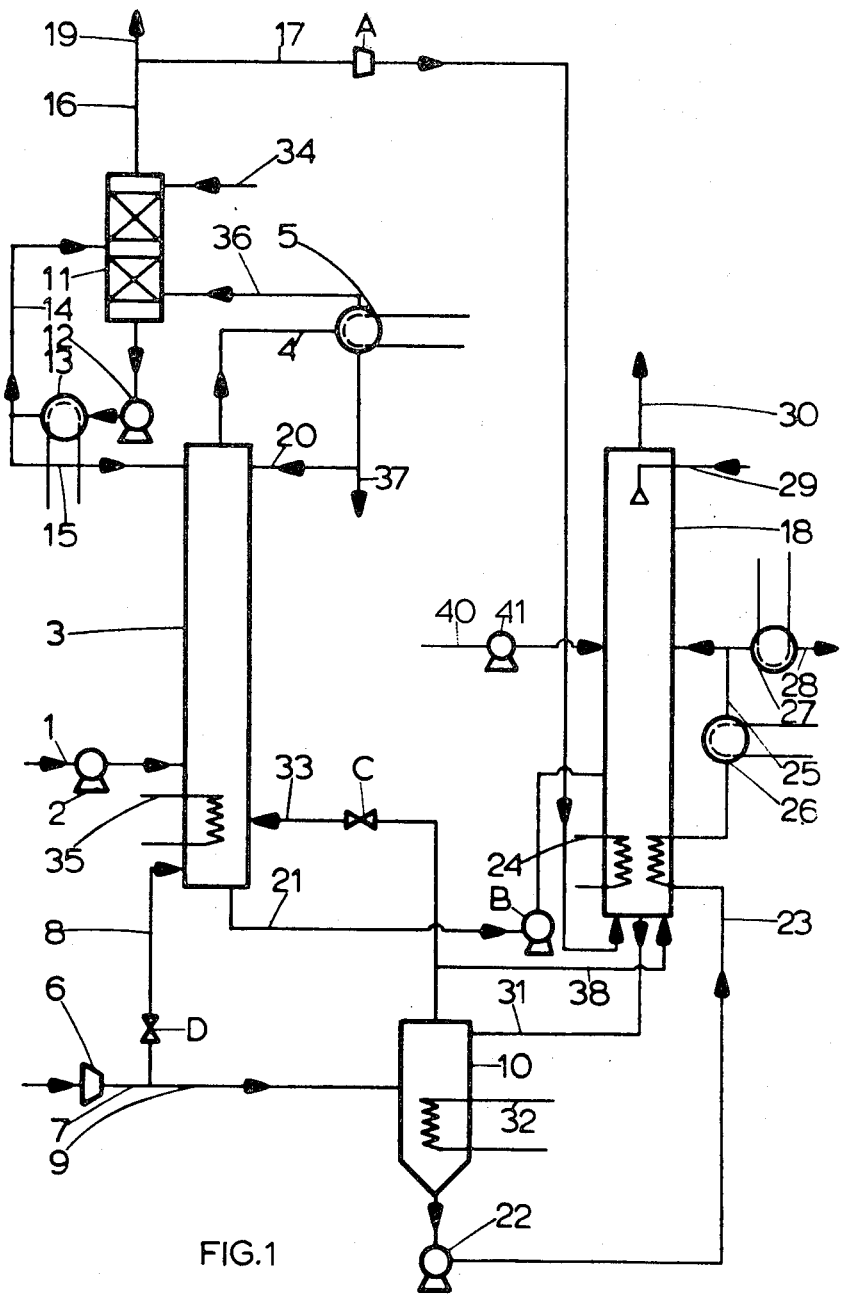
FIG. 1 schematically illustrates one embodiment of a process for the separation of ammonia and carbon dioxide which is utilized in accordance with the present invention for the removal of urea from urea-containing waste water.

Referring to FIG. 1, the mixture to be separated, containing ammonia, carbon dioxide and water, is fed through line 1 and pump 2 into ammonia separation zone 3, here illustrated as a rectifying column. If necessary, heat can be supplied to column 3 by means of heating coils 35. At the top of column 3, ammonia is discharged through line 4. Ammonia is condensed by deep cooling in condenser 5. An uncondensed gas mixture, composed of ammonia and inerts, leaves this condenser through line 36. The origin of the inert gases is the passivation air supplied to the equipment in order to keep the construction materials of the vessels and lines passivated so as to prevent unacceptable corrosion. Instead of air, it is, of course, possible to use for this purpose oxygen or a substance evolving oxygen. Part of the air is illustrated as being fed via compressor 6, lines 7 and 8, and pressure reducing valve D, to ammonia separation column 3, and part is fed through line 9 to desorber 10.

The gas leaving condenser 5 via line 36 is stripped of ammonia in washing column 11 by washing with water supplied through line 34. The resulting aqueous solution is discharged from washing column 11 by means of pump 12 and passed through recirculation cooler 13 to remove the heat of absorption. A part of the cooled liquid solution is returned to washer 11 through line 14. The remainder of the solution is returned to the ammonia rectification column through line 15.

The inert gas is discharged through line 16 and fed via line 17 to the bottom of the carbon dioxide separation zone 18, here illustrated as a rectification column. The insert gas is raised to a higher pressure in compressor A if a higher pressure is used in the carbon dioxide separation zone. If desired, the inerts may also be vented in whole or in part through line 19.

A portion of the ammonia liquidified in condensor 5 is returned through line 20 to the ammonia rectification column as reflux. The remainder is withdrawn through line 37.

From the bottom of the ammonia rectification column 3, the residual liquid phase containing ammonia, carbon dioxide and water is discharged through line 21 and fed into the carbon dioxide rectification column 18. Pump B is used if the carbon dioxide separation zone is operated at a higher pressure than the ammonia separation zone.

A quantity of urea-containing waste water to be purified is supplied to column 18 through line 40 and pump 41, which also functions as diluting water in the carbon dioxide separation zone. If desired, additional diluting water may be supplied from the residual liquid phase coming from the bottom of desorber 10 through pump 22 and lines 23 and 25.

A portion of the heat required for rectification in column 18 is obtained by allowing the residual liquid phase from the bottom of desorber 10 to liberate part of its heat into the bottom of column 18. The remainder of the heat required in the carbon dioxide rectification column 18 is here supplied through heating coils 24, e.g., in the form of steam. So as to improve heat distribution, a further portion of the heat content of the residual liquid phase from desorber 10 is removed in coolers 26 and 27, before the remaining portion of the residual liquid phase is discharged through line 28.

Through line 29, a flow of washing water is supplied to carbon dioxide rectification column 18 to remove, as much as possible, any remaining ammonia from the carbon dioxide. Carbon dioxide leaves the top of column 18 through line 30, possibly containing some inerts, but containing substantially no ammonia.

The residual liquid phase from the bottom of carbon dioxide rectification column 18, being a dilute solution of ammonia and carbon dioxide and water, and possibly also containing some residual urea, is passed through line 31 and into desorber 10 wherein any residual urea is hydrolyzed and nearly all of the ammonia and carbon dioxide is expelled by heating with, for instance, steam supplied through heating coils 32.

The residual liquid phase from desorber 10, which is substantially free of ammonia, carbon dioxide and urea, passes through line 23, in part to the carbon dioxide rectification column, and the remainder, after the above noted heat exchange, is discharged through line 28. A portion of the gaseous mixture of ammonia, carbon dioxide and water formed in desorber 10 passes through line 33 into the ammonia rectification column 3. Reducing valve C is utilized if the carbon dioxide separation zone is operated at a higher pressure then the ammonia separation zone. The remainder of this desorber gas mixture passes through line 38 into the bottom of the carbon dioxide rectification column.

Figure 2:
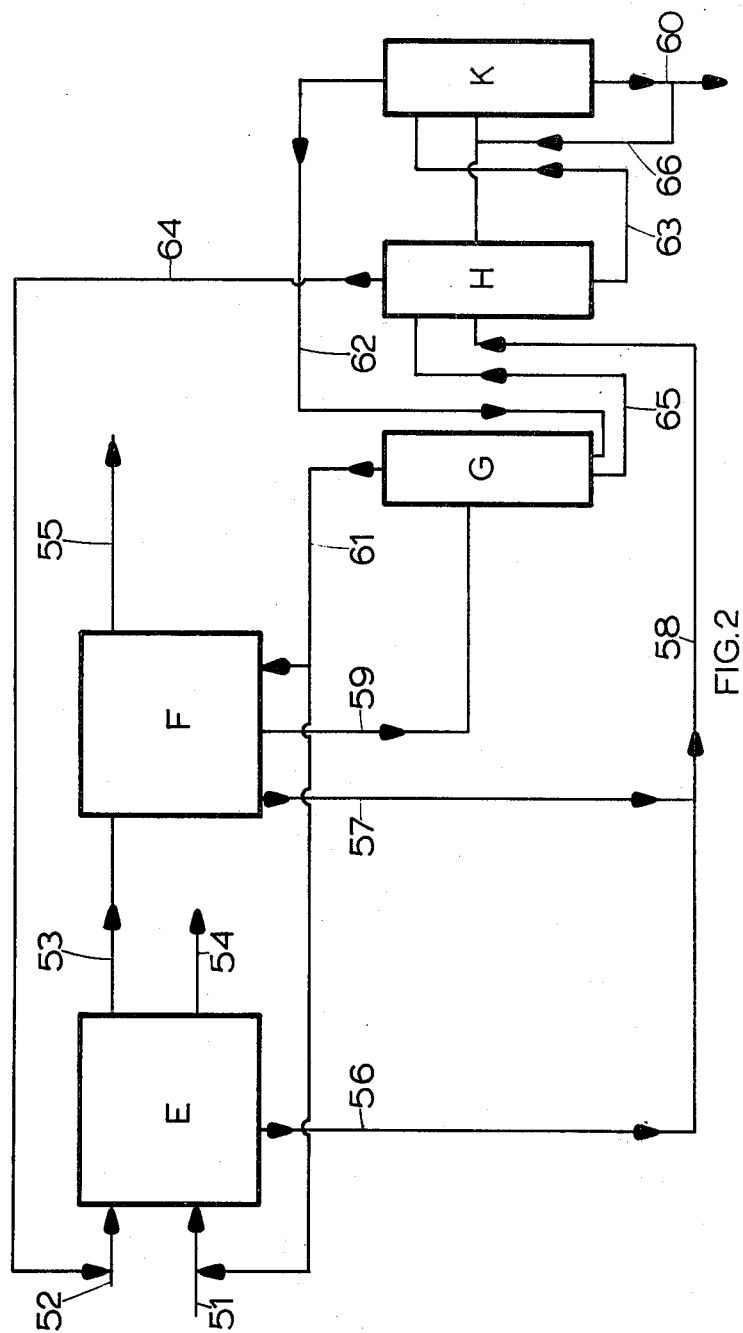
FIG. 2 is a schematically representation of the major processing units for the preparation of urea and melamine incorporating the improvement of this invention.

FIG. 2 is a block diagram of a process for the preparation of urea and melamine, combined with the process for the separation of ammonia and carbon dioxide together with the removal of urea and its hydrolysis products from a urea-containing waste water stream.

Through line 51 and 52, respectively, ammonia and carbon dioxide are fed into urea production unit E. Water-free urea is discharged from this urea production unit E through lines 53 and 54, respectively, to a melamine production unit F and, for instance, to storage or another application for urea (not shown).

From the melamine production unit F, product melamine is discharged through line 55. From melamine production F, and from urea production unit E, urea-containing waste water streams, that may also contain ammonia and carbon dioxide, are discharged through lines 57 and 56, respectively. These waste water streams are combined into line 58 and fed into an ammonia/carbon dioxide separation unit, schematically illustrated as units G, H and K. Additionally, a solution of ammonia and carbon dioxide in water is fed from the melamine production unit F to the ammonia/carbon dioxide separation unit through line 59.

In the ammonia/carbon dioxide separation unit, the ammonia separation zone is schematically represented by block G, the carbon dioxide separation zone by block H and the desorption zone by block K.

The ammonia and carbon dioxide solution from melamine production unit F is fed through line 59 into ammonia separation G, which is also fed with a gaseous mixture of ammonia, carbon dioxide and water vapor via line 62 from desorption zone K. From the top of ammonia separation zone G, ammonia, substantially free of carbon dioxide and water, is discharged through line 61 and partly recycled to urea unit E and partly to melamine unit F.

The residual liquid phase of ammonia, carbon dioxide and water from the bottom of ammonia separation zone G is fed to carbon dioxide separation zone H through line 65. Additionally, the urea-containing water originating from both the urea and melamine units is fed to carbon dioxide separation zone H through line 58. Also at the same time, a quantity of dilution water can be supplied to carbon dioxide separation zone H from the bottom of desorption zone K through line 66.

Carbon dioxide, substantially free of ammonia and water, is discharged from the top of carbon dioxide separation zone H through line 64, and may be recycled to urea unit E. The residual liquid phase from the bottom of carbon dioxide separation zone H, consisting of a dilute aqueous solution of ammonia and carbon dioxide, and which still may contain urea, is discharged through line 63 and fed into desorption zone K. In desorption zone K the urea is further hydrolyzed to ammonia and carbon dioxide, which, together with the ammonia and carbon dioxide fed to desorption zone K via line 63, is substantially all desorbed.

The resulting gas mixture of ammonia, carbon dioxide and water vapor from desorption zone K is fed via line 62 to ammonia separation zone G. The remaining water in desorption zone K, now containing only traces of ammonia, carbon dioxide and/or urea, is discharged through line 60.

EXAMPLE

In an installation such as illustrated in FIG. 1, ammonia, substantially free of carbon dioxide and water, and carbon dioxide, substantially free of ammonia and water, are separated from a mixture of ammonia, carbon dioxide and water, combined with the purification of a urea-containing effluent. The reference numerals referred to in this Example relate to FIG. 1, and all percentages given are by weight. The pressures are with respect to the ammonia/carbon dioxide/water system, i.e., the total partial pressure of those components. Due to the presence of inert gas, the actual pressure may be slightly higher.

At a pressure of 18 bar, 56,489 kg/h of a solution of ammonia and carbon dioxide in water is fed to the ammonia rectification column (3). The composition of this solution is 32.8% ammonia, 18.3% carbon dioxide and 48.9% water. By means of compressor (6), 635 kg/h of passivation air are supplied into the process, 248 kg/h of which is introduced into ammonia rectification column (3), and 387 kg/h of which is introduced into desorber (10).

Through line (33), 31,647 kg/h of a gas mixture consisting of 55.6% ammonia, 6.4% carbon dioxide, 38.0% water and 0.5% inerts, originating in desorber (10), is also supplied to ammonia rectification column (3). This gas mixture is expanded from the desorber pressure of 30 bar to the ammonia rectification column pressure by means of expansion valve C. From the top of ammonia rectification column (3), 45,455.7 kg/h of a gas mixture consisting of 98.6% ammonia, 0.1% water, and 1.2% inerts is discharged. Part of this gas mixture is liquified in condenser (5) by cooling, and part of this condensed liquid is recycled to column (3) as reflux. The remaining 19,497 kg/h of liquid ammonia is discharged from the process.

From condenser (5), 2,365 kg/h of a gas mixture consisting of 87.3% ammonia and 22.7% inerts is sent to scrubber (11) wherein it is scrubbed with water. Heat is removed from scrubber (11) by means of recirculation cooler (13). A solution of 4,229 kg is recycled to the ammonia rectification column per hour. Six hundred thirty-five kg/h of inert gas leave the top of scrubber (11) and are fed to carbon dioxide rectification column (18) through lines (16) and (17). This inert gas is compressed in compressor A to the system pressure of 30 bar utilized in the carbon dioxide rectification column.

From the bottom of the ammonia rectification column (3), 71,039 kg/h of liquid are fed to the carbon dioxide rectification column (18) through line (21) and pump B.

Carbon dioxide rectification column (18) is additionally fed with 10,852 kg/h of gas mixture originating in desorber (10) via line (38), and 35,994 kg/h of diluting water from desorber (10) through line (23). The diluting water from the desorber is substantially pure water containing only traces of ammonia, carbon dioxide and urea, and has a temperature of 231° C. when leaving the desorber. A portion of the heat in the desorber liquid is given off in the carbon dioxide rectification column through heating coils located in the bottom thereof.

The carbon dioxide rectification column is additionally fed through line (40) and pump (41) with a urea plant process stream or effluent consisting of 276 kg/h urea, 470 kg/h carbon dioxide, 811 kg/h ammonia and 19,697 kg/h of water.

At the top of carbon dioxide rectification column (18), 8,425 kg/h of scrubbing water is supplied, which serves to scrub out the last traces of ammonia from the carbon dioxide before it leaves the column. From the top of carbon dioxide rectification column (18), 11,623 kg/h of a gas mixture, consisting of 94.3% carbon dioxide and less than 100 ppm $NH_3$ is discharged.

The residual liquid phase leaving the bottom of column (18), consisting of 136,526 kg/h of a solution of 80.7% water, 17.3% ammonia and 2.0% carbon dioxide, and having a temperature of 181° C., is fed into desorber (10). The composition of this liquid is rich with respect to ammonia—that is, it is on the ammonia rich side of the boundary line. The solution is heated in desorber (10) using, e.g., steam, to hydrolyze any remaining urea, and to desorb substantially all of the ammonia and carbon dioxide. Of the 94,027 kg/h of water discharged from the desorber, 35,994 kg/h is used as diluting water in the carbon dioxide rectification column, and the remainder, 58033 kg/h, is discharged after cooling in cooler (27), and can be used, for example, for absorbing ammonia and carbon dioxide in other processing facilities such as utilized in the production of urea and/or melamine.

What is claimed is:

1. In a process for the removal of urea from urea-containing waste water by treating said waste water at elevated temperature and pressure to hydrolyze urea, and desorbing ammonia and carbon dioxide thus formed, the improvement comprising carrying out said urea removal in conjunction with the separation of ammonia and carbon dioxide from a process stream containing mixtures thereof by the steps of:

(a) separating, in an ammonia separation zone, an ammonia off-gas substantially free of carbon dioxide and water from a first residual liquid phase containing ammonia, carbon dioxide and water, and introducing said first residual liquid phase into a carbon dioxide separation zone;

(b) separating, in said carbon dioxide separation zone, a carbon dioxide off-gas substantially free of ammonia and water from a second residual liquid phase containing ammonia, carbon dioxide and water, and introducing said second residual liquid phase into a desorption zone; and (c) separating, in said desorption zone, an off-gas containing ammonia, carbon dioxide and water vapor from a third residual liquid phase substantially free of ammonia and carbon dioxide, and introducing at least a portion of said off-gas into said ammonia separation zone;

wherein said process stream and said urea-containing waste water are introduced into any of steps (a), (b) or (c).

2. The process of claim 1 wherein said desorption zone is operated at a pressure of between about 5 and 50 bar.

3. The process of claim 1 wherein said desorption zone is operated at a pressure of between 20 and 40 bar.

4. The process of claims 1, 2 or 3 wherein said urea-containing waste water is introduced into said carbon dioxide separation zone in step (b).

5. The process of claim 1 wherein said process is practiced in conjunction with a process for the preparation of melamine from urea and said process stream containing a mixture of ammonia and carbon dioxide is derived from said process from producing melamine.

6. In a process for the preparation of melamine by the catalytic conversion of urea in the presence of gaseous ammonia to form a gaseous reaction mixture containing melamine, ammonia and carbon dioxide, separation of melamine from the gaseous reaction mixture and thereafter forming an aqueous solution of ammonia and carbon dioxide from the remainder of such mixture, and separating the ammonia and carbon dioxide contained in such solution by the steps of:

(a) separating, in an ammonia separation zone, an ammonia off-gas substantially free of carbon dioxide and water from a first residual liquid phase containing ammonia, carbon dioxide and water, and introducing said first liquid residual phase into a carbon dioxide separation zone;

(b) separating, in said carbon dioxide separation zone, a carbon dioxide off-gas substantially free of ammonia and water from a second residual liquid phase containing ammonia, carbon dioxide and water, and introducing said second residual liquid phase into a desorption zone; and (c) separating, in said desorption zone, an off-gas containing ammonia, carbon dioxide and water vapor from a third residual liquid phase substantially free of ammonia and carbon dioxide, and introducing at least a portion of said off-gas into said ammonia separation zone;

wherein said aqueous solution is introduced into any of steps (a), (b) and (c), the improvement comprising additionally introducing into said carbon dioxide separation zone a urea-containing waste water stream and substantially completely hydrolyzing said urea, and separating the resulting ammonia and carbon dioxide in said steps (a), (b) and (c).

7. The process of claim 6 wherein said process is carried out in conjunction with a process for the synthesis of urea from ammonia and carbon dioxide at an elevated temperature and pressure to produce an aqueous solution of urea, concentrating said aqueous urea solution by evaporation of water thereby forming a vapor phase containing water, ammonia, carbon dioxide and urea, condensing said vapor phase to form said urea-containing waste water introduced into said carbon dioxide separation zone, and utilizing at least a portion of the concentrated urea for the production of said melamine.

* * * * *